United States Patent [19]

Gernhart et al.

[11] Patent Number: 4,821,579

[45] Date of Patent: Apr. 18, 1989

[54] APPARATUS FOR CLAMPING A TEST SAMPLE IN A TESTING MACHINE

[75] Inventors: Peter Gernhart, Klingenberg; Gerhart Hintz, Rossdorf; Guenter Keller, Modautal; Andreas Pohl, Klein Umstadt, all of Fed. Rep. of Germany

[73] Assignee: Carl Schenck AG, Darmstadt, Fed. Rep. of Germany

[21] Appl. No.: 207,758

[22] Filed: Jun. 16, 1988

[30] Foreign Application Priority Data

Jun. 19, 1987 [DE] Fed. Rep. of Germany ....... 3720303

[51] Int. Cl.$^4$ .............................................. G01N 3/06
[52] U.S. Cl. ......................................... 73/856; 73/834
[58] Field of Search ................. 73/834, DIG. 11, 821, 73/826, 856, 859; 356/32, 152

[56] References Cited

U.S. PATENT DOCUMENTS

| 3,102,421 | 9/1963 | Cosner et al. .............. 73/837 X |
| 3,592,545 | 7/1971 | Paine ............................. 73/826 X |
| 4,605,857 | 8/1986 | Ninomiya et al. . | |

FOREIGN PATENT DOCUMENTS

| 0023643 | 2/1981 | European Pat. Off. . |
| 0194354 | 9/1986 | European Pat. Off. . |
| 0255552 | 2/1988 | European Pat. Off. . |
| 1773642 | 1/1974 | Fed. Rep. of Germany . |
| 2330162 | 12/1974 | Fed. Rep. of Germany . |
| 2602583 | 7/1976 | Fed. Rep. of Germany . |
| 2631663 | 1/1978 | Fed. Rep. of Germany . |
| 3151542 | 7/1983 | Fed. Rep. of Germany . |
| 3346429 | 7/1985 | Fed. Rep. of Germany . |
| 3422988 | 1/1986 | Fed. Rep. of Germany . |
| 895600 | 5/1962 | United Kingdom . |
| 1294234 | 10/1972 | United Kingdom . |

OTHER PUBLICATIONS

Journal of Scientific Instruments (Journal of Physics E) 1969 Series 2, vol. 2; pp. 375–377, Article Entitled: "The Application of a Light-Sensitive Potentiometer in the Measurement of the Mechanical Properties of Single Fibers".

Primary Examiner—Jerry W. Myracle
Attorney, Agent, or Firm—W. G. Fasse; D. H. Kane, Jr.

[57] ABSTRACT

In a test sample clamping apparatus for testing machines, having a clamping head or chuck and a force sensor (2) arranged on the chuck, testing forces are measured with a force sensor and displacements or test sample deformations are measured simultaneously with a light deflection. Thus, rapid test procedures such as fast tensile rupture tests are made possible. The clamping head or chuck includes a base plate (3), one side of which receives or holds clamping elements (15) and the other side of which clamps down the force sensor (2) against a support. A mirror surface (8, 8') is arranged on the base plate (3) or on other appropriate surfaces of the clamping head so as to reflect a light beam (10) emitted by a light source (9) onto a position detector (11). In order to measure a deformation caused displacement of the clamping head and correspondingly of the test sample (4), an electronic evaluating circuit (12) evaluates the position dependent output signal of the detector (11).

5 Claims, 1 Drawing Sheet

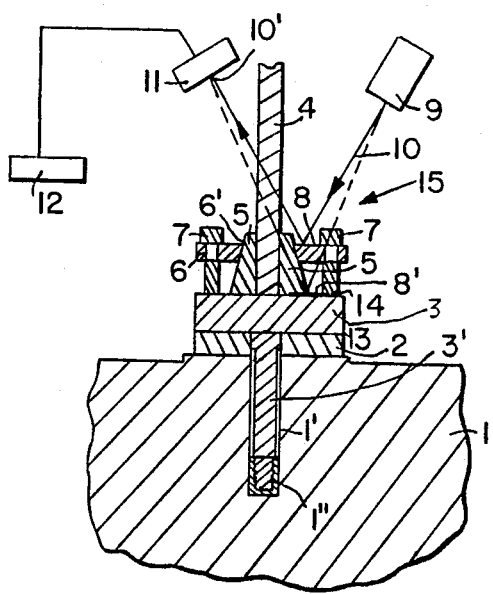

APPARATUS FOR CLAMPING A TEST SAMPLE IN A TESTING MACHINE

CROSS-REFERENCE TO RELATED APPLICATIONS

The present application relates to U.S. Ser. No.: 207,754, filed on the same date as the present application; and U.S. Ser. No.: 207,729, also filed concurrently with the present application.

FIELD OF THE INVENTION

The invention relates to an apparatus for clamping a test sample in a testing machine, especially for fast tensile rupture testing machines having a clamping head or chuck and a force measuring device such as a load cell arranged on the chuck. The force measuring device is connected to a stationary rigid part or to a movable part of the testing machine.

DESCRIPTION OF THE PRIOR ART

As disclosed in the German Patent Publication (DE-PS) No. 1,773,642, it is known to arrange a force measuring device on the test sample clamping head or chuck of testing machines such as tensile testing machines. The force measuring device is usually attached to a cross yoke or to a cross girder of the testing machine and is then further connected to the clamping head or chuck.

In testing situations requiring a very rapid testing cycle, for example, in fast tensile rupture tests, it has not been previously possible to sufficiently accurately determine the force characteristic and the path distance or displacement characteristic with simple means and in a simple manner during the short time duration of the testing procedure. The mass of the components, including the clamping means and the force measuring arrangement, leads to low fundamental characteristic frequencies or eigenfrequencies in the force measuring procedure. These low fundamental characteristic frequencies hinder or even make it impossible to measure high frequency phenomena. Furthermore, in these cases using previously known methods, it was not possible to carry out a direct distance or displacement measurement near the test sample.

OBJECTS OF THE INVENTION

In view of the foregoing it is the aim of the invention to achieve the following objects singly or in combination:

to construct a test sample clamping arrangement for testing machines by means of which force and displacement measurements may be carried out simultaneously by simple means, especially in connection with fast tensile rupture tests;

to achieve a high accuracy of measurement of both the force characteristic and the deformation or displacement characteristic, especially during a rapid test procedure in such a testing machine;

to integrate or combine a lightweight force measuring device with a distance or displacement measuring device in a clamping head or chuck of such a testing machine;

to reduce the mass of a test sample clamping arrangement through integration and combination of the components, in order to increase the fundamental characteristic frequency of the clamping and measuring arrangement so that high frequency test procedures may be accurately performed; and to carry out a direct deformation or distance measurement very near the test sample so as to achieve a high accuracy in such a measurement.

SUMMARY OF THE INVENTION

The above objects have been achieved by a test sample clamping apparatus for testing machines of the general type described above according to the invention in that the clamping head or chuck for the test sample includes a base plate for the clamping elements. One side of the base plate is constructed for receiving said clamping elements, while the other side of the base plate is constructed for the attachment of the force measuring device or load cell. The base plate clamps the force measuring device or load cell against a support such as a cross-girder, table, platform, or the like of the testing machine which acts as a counter bearing member. At least one mirror surface is arranged on the base plate or on some other appropriate surface of the clamping head. A light source provides a light beam which is reflected by the mirror surface onto a beam position detector. The detector generates an output signal which is applied as an input to an electronic evaluating circuit for the purpose of measuring the deformation of the test sample. The force measuring or load cell device is, for example, a piezoelectric measuring ring which is relatively stiff in the effective direction of the force to be measured. The light beam is preferably emitted by a laser light source.

By means of the combination of a lightweight force measuring device with a path or distance (deformation) measuring device, both integrated into the clamping arrangement of a testing machine, considerably improved measurement results are achievable, for force measurement as well as for displacement or distance or deformation measurements, especially for rapid testing procedures. Furthermore, the fundamental characteristic frequency of the clamping arrangement is considerably increased because the mass or weight of the arrangement is considerably reduced in comparison to previously known arrangements, by the special arrangement of the base plate which, on the one hand, is a component of the clamping head or chuck, and on the other hand, is a component of the force receiver or force measuring device.

BRIEF DESCRIPTION OF THE DRAWING

In order that the invention may be clearly understood, it will now be described, by way of example, with reference to the accompanying drawing, wherein the single FIGURE is a sectional side view of a clamping head arrangement according to the invention attached to a cross girder of a testing machine.

DETAILED DESCRIPTION OF PREFERRED EXAMPLE EMBODIMENTS AND OF THE BEST MODE OF THE INVENTION

As shown in the Figure, a lightweight force measuring device or sensor or load cell 2 which may, for example, be a piezoelectric measuring ring, is clamped against a cross girder 1 of a material testing machine by means of a base plate 3. The cross girder 1 forms a counter bearing or support which may take several different specific forms. Hence, it is only shown in a general manner. The force sensor 2 is attached or clamped-in such a manner that compressive forces as well as tensile forces can be transmitted and measured by means of the clamping arrangement according to the invention. For example, the clamping may be achieved by means of a tension screw 3' passing through the center of the base plate 3 and extending into a bore 1' in the cross girder 1. At least the lower end of the bore 1' is threaded at 1" to receive and engage the tension or clamping screw 3'. Thus, the base plate 3 is screwed down by means of the screw 3' in order to clamp down the force sensor 2. The shape of the bottom surface 13 of the base plate 3 is suitably adapted for receiving or mating with the force sensor 2, whereby the base plate 3 becomes a component of the force sensing means.

A clamping device 15 which actually receives and clamps the test sample 4 is arranged on the top surface 14 of the base plate 3. The clamping device 15 includes clamping jaws 5 which may, for example, be wedge shaped. In order to clamp or mount the test sample 4 for testing, the clamping jaws 5 are brought into tight clamping engagement with the test sample 4 by tightening screws 7 which clamp down on a clamping yoke 6. The screws 7 are threaded into appropriate threaded holes in the base plate 3. The clamping yoke 6 has a conical hole or at least angled wall surfaces 6' having a corresponding slope angle for receiving the several clamping jaws 5. Thus, as the clamping yoke 6 is screwed down by means of the screws 7, the angled wall surfaces 6' clamp the clamping jaws 5 radially together to tightly grip the test sample 4.

A mirror surface 8 is arranged on the clamping yoke 6. Alternatively, a mirror surface 8' may be arranged on the base plate 3.

The mirror surface 8 or 8' is used for achieving a path or deformation length measurement of the test sample 4 in the clamping arrangement device 15. A light beam 10 emitted by a light source 9, for example a laser light source 9, is directed onto the mirror surface 8 or 8' from which it is reflected toward a position detector 11. The position detector 11 is a photoelectric position sensor which is able to determine the exact location or position of a point of light 10' impinging on the surface of the detector. A detector of the type S1352 manufactured by Hamamatsu is suitable for this purpose. The position detector 11 generates a photoelectric current which is dependent upon the location of a point of light 10' impinging on the detector surface. The respective output signal of the photodetector 11 is evaluated in an electronic evaluating circuit 12, for example, as a voltage signal proportional to the position or location of the point of light 10' impinging on the position detector 11. The evaluating circuit 12 may be of the type MV319 manufactured by C. Schenck AG or the circuit of FIG. 7 of Dr. Seitner/Hamamatus pamphlet 26.5 . . . 0.0883. Movement of the mirror surface 8 or 8' causes movement of the point of light 10' impinging on the detector 11, whereby this moving position is determined by the detector 11 and evaluated in the circuit 12. The determined movement of the point of light 10' is a direct measure for the movement of the mirror surface 8 or 8' and thus correspondingly for the movement of the test sample 4. Because the mirror surface 8 or 8' is quite lightweight, and because the point of light 10' responds essentially instantaneously to any movement of the mirror surface 8 or 8', exact displacement or deformation measurements may be carried out especially for rapid test procedures, such as rapid tensile burst tests.

A force applying device not shown is secured in a conventional manner to the upper end of the test sample for applying the testing force or load to the test sample 4. The sensing mirror may be attached to any location which responds to the application of force to the test sample in such a way that the response moves the mirror so that the light beam is correspondingly moved, thereby providing information regarding the deformation or displacement of the test sample caused by the force application. The applied force itself is, in all instances measured by the sensor 2. It is possible to keep the mirror stationary and to move the light source and the sensor in synchronism with the movement or deformation of the test sample. The movement of the point of light 10' and the signal evaluation would be the same as described above where the mirror is attached to the clamping device.

Although the invention has been described with reference to specific example embodiments, it will be appreciated, that it is intended to cover all modifications and equivalents within the scope of the appended claims.

What we claim is:

1. A clamping apparatus for a test sample in a testing machine especially for carrying out fast tensile rupture tests, comprising a clamping chuck, force sensor means for measuring a force, a base plate comprising a first side for mounting said clamping chuck and a second side for mounting said force sensor means, said base plate comprising means for securing said force sensor means to counter support means of said testing machine, said clamping arrangement further comprising reflector means, a light source emitting a light beam, a photo-position detector, and electronic signal evaluating circuit means connected to said photo-position detector, said reflector means being arranged to reflect said light beam toward and onto said photo-position detector for providing a displacement representing signal to said electronic evaluating circuit means to evaluate said displacement representing signal and determine a measurement of a deformation of said test sample.

2. The clamping apparatus of claim 1, wherein said reflector means is arranged on said base plate.

3. The clamping apparatus of claim 1, wherein said reflector means comprises a flat mirror surface.

4. The clamping apparatus of claim 1, wherein said force sensor means comprises a piezoelectric measuring ring which is relatively stiff in the direction of the effective testing forces.

5. The clamping apparatus of claim 1, wherein said light source comprises a laser light source, and said light beam has a point cross-section.

* * * * *